United States Patent [19]
Hayashi

[11] Patent Number: 5,462,967
[45] Date of Patent: Oct. 31, 1995

[54] FEED ADDITIVE FOR LIVESTOCK AND FEED FOR LIVESTOCK

[75] Inventor: Masaharu Hayashi, Wakayama, Japan

[73] Assignee: Kao Corporation, Tokyo, Japan

[21] Appl. No.: 899,315

[22] Filed: Jun. 16, 1992

[30] Foreign Application Priority Data

Jun. 17, 1991  [JP]  Japan ................... 3-144654

[51] Int. Cl.⁶ .............. A61K 31/225; A61K 31/23; A61K 31/20
[52] U.S. Cl. .............. 514/547; 514/552; 514/560; 514/561; 514/558; 514/559; 426/2
[58] Field of Search .................. 514/560, 561, 514/558, 559, 547, 552; 426/2, 72

[56] References Cited

U.S. PATENT DOCUMENTS

| | | | |
|---|---|---|---|
| 3,658,548 | 4/1972 | Haas | 426/72 |
| 3,952,107 | 4/1976 | Shibata | 514/547 |
| 4,002,775 | 1/1977 | Kabara | 426/532 |
| 4,223,040 | 9/1980 | Carroll | 514/558 |
| 4,961,934 | 10/1990 | Iwasaki et al. | 426/2 |

FOREIGN PATENT DOCUMENTS

| | | | |
|---|---|---|---|
| 62-210975 | 9/1987 | Japan | A23P 1/06 |
| 1215247 | 8/1989 | Japan | A23K 1/16 |
| 2177865 | 7/1990 | Japan | A23K 1/18 |
| 2261350 | 10/1990 | Japan | A61K 1/18 |
| 3198748 | 8/1991 | Japan | A23K 1/16 |
| 3244349 | 10/1991 | Japan | A61K 31/22 |

*Primary Examiner*—Raymond Henley, III
*Assistant Examiner*—Kevin Weddington
*Attorney, Agent, or Firm*—Sughrue, Mion, Zinn, Macpeak & Seas

[57] ABSTRACT

A feed additive which is effective for preventing and/or treating protozoiasis of livestock such as coccidiosis and for suppressing accumulation of fat of livestock is disclosed, which comprises (a) a triglyceride of a medium-chain fatty acid having 6 to 12 carbon atoms; and (b) at least one substance selected from a medium-chain fatty acid having 6 to 12 carbon atoms, a monoglyceride of the fatty acid and a diglyceride of the fatty acid. A feed for livestock containing the feed additive, and a method for preventing and/or treating protozoiasis of livestock and a method for suppressing excess accumulation of fat of livestock using the feed are also disclosed. The feed and method of the present invention are particularly effective for broiler.

8 Claims, No Drawings

FEED ADDITIVE FOR LIVESTOCK AND FEED FOR LIVESTOCK

FIELD OF THE INVENTION

This invention relates to a feed additive for livestock and a feed for livestock. More particularly, it relates to a feed additive for livestock and a feed for livestock having antiprotozoiasis effect and which is effective in suppressing an excess formation of systemic fat of, in particular, broiler (domestic fowl).

BACKGROUND OF THE INVENTION

In these days, so-called concentrated feeds for livestock of a high protein content and a high energy value are preferred in order to elevate feed efficiency. However, it has been found out that feeding with these concentrated feeds would deteriorate the function of the liver, which acts an important role in nutritional metabolism, so that it induces enlargement of liver or yellow hepatization and, furthermore, cause the abnormal accumulation of fat which induces fatty liver or deterioration in meat qualities due to excessively high fat content. In order to solve these problems, JP-A-1-215247 (the term "JP-A" as used herein means an "unexamined published Japanese patent application.) provides a feed for livestock whereby triglycerides of medium-chain fatty acids having 6 to 12 carbon atoms are fed to livestock to thereby reduce the accumulation of excessive fat and to efficiently utilize energy.

In recent years, on the other hand, the livestock industry has been tending toward intensive systems with an increase in feeding density and the enlargement of feeding scale. As a result, livestock industry can be managed under the factory system, which makes it possible to stably supply animal products over a long period of time. However, environmental management is worsened as the livestock industry becomes intensive. Consequently there arises a serious problem, i.e., the outbreak of diseases.

Examples of protozoan diseases, from among the above-mentioned ones, include coccidiosis, leucocytozoonosis, trypanosomiasis and leishmaniasis. In order to prevent and treat these diseases, there have been used various drugs (for example, sulfa drugs, quinoline derivatives, nucleic acid derivatives, quinazoline derivatives, guanidine derivatives, folic acid antagonists, polyether antibiotics). However, these drugs are expensive and have a highly restricted safety range, which makes it troublesome to add a large amount of them to feeds for livestock.

SUMMARY OF THE INVENTION

The present inventors have conducted extensive studies in order to solve the above-mentioned problems. As a result, they have successfully found that an excellent effect of preventing and treating protozoiasis diseases, in particular, coccidiosis, can be obtained and an excess fat accumulation in broilers (domestic fowl) can be reduced so that the feed efficiency can be improved by adding a mixture of a conventional triglyceride of a medium-chain fatty acid having 6 to 12 carbon atoms with at least one substance selected from a medium-chain fatty acid having 6 to 12 carbon atoms, a monoglyceride of the fatty acid and a diglyceride of the fatty acid, thus completing the present invention.

Accordingly, the present invention provides a feed additive for livestock which comprises the following components (a) and (b): (a) triglycerides of medium-chain fatty acids having 6 to 12 carbon atoms (for example, caproic acid, caprylic acid, capric acid, lauric acid) (hereinafter referred to simply as "MCT"); and (b) at least one substance selected from among medium-chain fatty acids having 6 to 12 carbon atoms (hereinafter referred to simply as "MCFA"), monoglycerides of the fatty acids (hereinafter referred to simply as "MCM") and diglycerides of said fatty acids (hereinafter referred to simply as "MCD"), as well as a feed for livestock containing from 0.5 to 20% by weight of the feed additive for livestock.

The present invention further provides a method for preventing and/or treating protozoiasis of livestock which comprises the step of feeding a feed containing the feed additive.

The present invention still furthermore provides a method for suppressing an excess accumulation of fat of livestock which comprises the step of feeding a feed containing the feed additive.

DETAILED DESCRIPTION OF THE INVENTION

The feed additive of the present invention may be given to various livestock (for example, fowls such as chicken breed fowl, egg-laying fowl and sire fowl; beef cattle, dairy cattle; pig (swine); sheep; goat; and infant animals thereof). It is particularly recommended to feed animals frequently infected with protozoiasis diseases, in particular, coccidiosis with the feed for livestock of the present invention. Although the feed additive for livestock and the feed for livestock of the present invention are effective on coccidiosis, it is expected that they would also exert preventive and treating effects on leucocytozoonosis and trypanosomiasis which differ from coccidiosis in infection pathway. Furthermore, the feed additive and the feed of the present invention are effective in reducing systemic fat and elevating resistance against protozoiasis diseases in broiler (domestic fowl).

MCT, MCFA, MCM and MCD to be used in the present invention may comprise each either a single fatty acid having 6 to 12 carbon atoms or a mixture thereof. MCFA, MCM and MCD to be mixed with MCT may be either a single compound or a mixture. In the present invention, the combination of MCT with the MCFA, MCM and MCD, each having a carbon atom number falling within the same range as that of MCT and carrying OH group(s), makes it possible to give a feed additive which is superior in antiprotozoiasis effects to a conventional additive comprising MCT alone. Further, MCFA, MCM and MCD comprising a fatty acid having 8 to 10 carbon atoms are preferably employed in the present invention.

In the feed additive of the present invention, a weight ratio of (a) MCT to (b) MCFA, MCM and MCD may be arbitrarily selected. The weight ratio of (a)/(b) preferably ranges from 10/90 to 90/10, more preferably from 10/90 to 50/50. When this weight ratio is smaller than 10/90, the weight-gain effect of MCT cannot sufficiently be achieved. When it exceeds 90/10, on the other hand, little antiprotozoiasis effect is observed.

In the feed for livestock of the present invention, the total content of (a) MCT and at least one of MCFA, MCM and MCD may range from 0.5 to 20% by weight, preferably from 1 to 10% by weight, based on the total feed.

A suitable amount of the total of (a) MCT and (b) at least one of MCFA, MCM and MCD to be fed per day per kilogram of the body weight of livestock can range from 1 to 600 g, though it may vary depending on the kind, the sex and the stage of growth of livestock. In particular, from 1 to 300 g, preferably 10 to 30 g, of the total of (a) MCT and (b) at least one of the MCFA, MCM and MCD are preferably fed per day per kilogram of the body weight in the case of beef cattle; from 2 to 600 g, preferably from 20 to 60 g, in the case of swine; and from 1 to 300 g, preferably from 10 to 30 g, in the case of broiler (domestic fowl).

The feed for livestock of the present invention further contains components commonly employed in the conventional feed for livestock examples of which include cereals (for example, corn, wheat, barley, rye, milo), brans (for example, rice bran, wheat bran, barley bran), cakes (for example, soybean oil cake, corn gluten meal, molasses), animal feed components (for example, fish meal, skim milk powder, whey, yellow grease, tallow) and nutrients (for example, vitamins, minerals). In the present invention, the above-mentioned feed additive may be used either as a substitute for conventional oily components or as a novel component to thereby achieve the objects of the present invention. When the feed additive is used as a substitute for oily components, the resulting feed exerts an excellent effect of reducing systemic fat. When the additive is used as a novel component together with other oily components, the resulting feed shows a high ratio of ingestion and achieves a high rate of gain.

The feed of the present invention may comprise the above-mentioned feed additive and other components at the ratio, for example, as specified below.

Typical example of formulation

| (Concentrated feed) | |
|---|---|
| (For Cattle) | |
| corn | 15 to 50% by weight |
| milo | 5 to 30% by weight |
| barley | 0 to 20% by weight |
| soybean oil cake | 0 to 40% by weight |
| wheat bran | 0 to 20% by weight |
| alfalfa meal | 0 to 20% by weight |
| molasses | 0 to 10% by weight |
| minerals | 0 to 5% by weight |
| vitamins | 0 to 3% by weight |
| feed additive | 0.5 to 10% by weight |
| (For Swine) | |
| corn | 20 to 80% by weight |
| milo | 0 to 40% by weight |
| barley | 0 to 30% by weight |
| wheat bran | 0 to 20% by weight |
| soybean oil cake | 0 to 10% by weight |
| fish meal | 0 to 10% by weight |
| defatted rice bran | 0 to 15% by weight |
| alfalfa meal | 0 to 10% by weight |
| molasses | 0 to 10% by weight |
| minerals | 0 to 3% by weight |
| vitamins | 0 to 3% by weight |
| feed additive | 0.5 to 20% by weight |
| (For Fowl) | |
| corn | 20 to 80% by weight |
| milo | 0 to 40% by weight |
| soybean oil cake | 0 to 40% by weight |

| -continued | |
|---|---|
| (Concentrated feed) | |
| fish meal | 0 to 10% by weight |
| corn gluten meal | 0 to 10% by weight |
| alfalfa meal | 0 to 10% by weight |
| meat-bone meal | 0 to 10% by weight |
| minerals | 0 to 3% by weight |
| vitamins | 0 to 3% by weight |
| feed additive | 0.5 to 20% by weight |

The feed for livestock of the present invention can be fed to livestock in either a solid form or an aqueous solution (liquid feeding). In the case of broiler (domestic fowl), the feed of the present invention is preferably fed in a dried powder form. To formulate the feed into a solid form, starch and the like can be further incorporated thereinto if necessary, and the resulting feed can be given to livestock as such. Alternatively, an aqueous solution can be prepared by adding the feed of the present invention into water so as to give a 15 to 30% by weight aqueous solution, and then mixing and kneading the resulting solution.

To further illustrate the present invention in greater detail, and not by way of limitation, the following Examples will be given.

EXAMPLE 1

A formula feed for broiler (domestic fowl) shown in Table 1 was prepared. In Table 1, the feeds of Test lot are according to the present invention, while the feeds of "Comparison lot" and "Control lot" are comparison with the present invention. Broilers (domestic fowls) (each lot having 5 birds) were preliminarily fed with each feed at liberty until 8-day age. On the 8th day, these birds were orally infected with $1 \times 10^5$ *Eimeria tenella* strain. After measuring the oocyst excretion for 8 days, the broilers were dissected and lesions in the cecum mucosae were observed. The results are shown in Table 2.

As a result, the oocyst excretion was remarkably reduced and scarcely any lesion was observed in the cecum mucosae of the bird fed with the feed according to the present invention as shown by Table 2. Thus, it is evident that the feeding with the feed according to the present invention would considerably suppress the outbreak of coccidiosis.

TABLE 1

| Component (% by weight) | Test lot I | Test lot II | Test lot III | Test lot IV | Test lot V | Comparison lot I | Comparison lot II | Control lot I | Control lot II |
|---|---|---|---|---|---|---|---|---|---|
| Corn | 60 | 60 | 60 | 60 | 60 | 60 | 60 | 60 | 60 |
| Soybean cake | 25 | 25 | 23 | 23 | 25 | 25 | 25 | 25 | 25 |
| Fish meal | 6.0 | 6.0 | 6.0 | 6.0 | 6.0 | 6.0 | 6.0 | 6.0 | 6.0 |
| Alfalfa meal | 0.5 | 0.5 | 0.5 | 0.5 | 0.5 | 0.5 | 0.5 | 0.5 | 0.5 |
| Calcium carbonate | 1.5 | 1.5 | 1.5 | 1.5 | 1.5 | 1.5 | 1.5 | 1.5 | 1.5 |
| Common salt | 0.3 | 0.3 | 0.3 | 0.3 | 0.3 | 0.3 | 0.3 | 0.3 | 0.3 |
| Mineral mix | 1.0 | 1.0 | 1.0 | 1.0 | 1.0 | 1.0 | 1.0 | 1.0 | 1.0 |
| Vitamin mix | 0.7 | 0.7 | 0.7 | 0.7 | 0.7 | 0.7 | 0.7 | 0.7 | 0.7 |
| Yellow grease | — | — | — | — | — | — | — | 5.0 | 5.0 |
| Beef tallow | — | — | — | — | 1.5 | — | — | — | — |
| Component (a)*1 | 4.0 | 2.5 | 1.5 | 4.75 | 1.0 | 5.0 | 1.0 | — | — |
| Component (b)*2: | | | | | | | | | |
| Invention: | | | | | | | | | |
| A | 1.0 | — | — | — | — | — | — | — | — |
| B | — | 2.5 | — | 0.25 | 2.5 | — | — | — | — |
| C | — | — | 5.5 | — | — | — | — | — | — |
| Comparison: | | | | | | | | | |
| D | — | — | — | — | — | — | 4.0 | — | — |

Notes;
*1MCT; $C_8/C_{10}$ = 85/15 (by weight, the same will be applied hereinafter)
*2Component (b):
A: MCFA of $C_6$–$C_{12}$; $C_6/C_8/C_{10}/C_{12}$ = 10/50/30/10.
B: MCFA of $C_6$–$C_{12}$/MCM of $C_6$–$C_{12}$/MCD of $C_6$–$C_{12}$ = 10/30/60 (in each case, $C_6/C_8/C_{10}/C_{12}$ = 10/40/30/20)
C: MCM of $C_8$–$C_{10}$/MCD of $C_8$–$C_{10}$ = 45/55 (in each case, $C_8/C_{10}$ = 60/40)
D: fatty acids of $C_{16}$–$C_{18}$/monoglycerides of fatty acids of $C_{16}$–$C_{18}$/diglycerides of fatty acids of $C_{16}$–$C_{18}$ = 10/40/50 (in each case, $C_{16}/C_{18}$ = 55/45)

Each of the carbon atom numbers of MCT, MCM and MCD means the number of carbon atoms in fatty acid residues excluding those involved in the glycerol skeleton. The same MCT and the additives A to D were employed in the following Examples.

TABLE 2

| | Oocyst excretion | | | Cecum lesion score*3 | Rate of gain*4 |
|---|---|---|---|---|---|
| | 6th day | 7th day | 8th day | | |
| Test lot | | | | | |
| I | $1.2 \times 10$ | $1.2 \times 10$ | $1.5 \times 10$ | 0.6 | 98.6 |
| II | $10^1>$ | $0.9 \times 10$ | $1.5 \times 10$ | 0.6 | 99.4 |
| III | $10^1>$ | $10^1>$ | $10^1>$ | 0.2 | 101.8 |
| IV | $10^2$ | $10^2$ | $0.9 \times 10^3$ | 1.0 | 97.7 |
| V | $10^1>$ | $10^1>$ | $3.0 \times 10$ | 0.7 | 104.9 |
| Comparative lot: | | | | | |
| I | $10^3$ | $10^3$ | $1.8 \times 10^3$ | 1.8 | 75.8 |
| II | $10^3$ | $10^5$ | $3.5 \times 10^5$ | 3.0 | 68.9 |
| Control lot*5: | | | | | |
| I | $10^1>$ | $10^1>$ | $10^1>$ | 0 | 100 |
| II | $9.4 \times 10^7$ | $18.1 \times 10^7$ | $109.4 \times 10^7$ | 4.0 | 42.5 |

Notes;
*3cecum lesion score; cecum lesion score for *E. tenella*-infected fowls (Johnson and Reid).
Criteria
0: No lesion was observed. Few spots of hemorrhage in cecum wall was observed.
+1: No thickening in cecum wall was observed and cecum contents was normal. Hemorrhage spots were increased and sometimes contain blood in cecum contents.
+2: Somewhat thickening in cecum wall was observed, but cecum contents were normal.
+3: Severe thickening in cecum wall, serious hemorrhage and blood masses in cecum were observed. Cecum contents were decreased. Serious expansion of cecum wall, serious hemorrhage and large cheese-like masses were observed. Cecum contents disappeared or were incorporated in the masses.
+4: Bird which showed the symptom died.
*4Rate of gain: calculated by referring the gain of the control lot I as to 100

*5Control lots: I: non-infected
II: infected

EXAMPLE 2

Formula feeds for fowl of Table 3 (for the first half, i.e., 0 to 21 day-age) and Table 4 (for the second half, i.e., from 21 to 57-day age) were prepared. In Tables 3 and 4, the feeds of "Test lot" are according to the present invention, while the feeds of "Comparison lot" are comparison with the present invention. Each 25 birds of 0-day age Chunkey male chickens were fed up to 57-day age with the feeds. On the final day of the feeding, 6 birds of each lot were dissected and the body weight, the weight of fat tissue in the abdominal cavity (hereinafter called abdominal fat) and feed conversion rate were determined.

As Table 5 shows, good results were achieved in all of the examined items in Test lots.

TABLE 3

| Component (% by weight) | Test lot I | Test lot II | Test lot III | Test lot IV | Comparison lot I | Comparison lot II |
| --- | --- | --- | --- | --- | --- | --- |
| Corn | 54.5 | 54.5 | 54.5 | 54.5 | 54.5 | 54.5 |
| Milo | 10.0 | 10.0 | 10.0 | 10.0 | 10.0 | 10.0 |
| Soybean cake | 21.2 | 21.2 | 21.2 | 21.2 | 21.2 | 21.2 |
| Fish meal | 7.5 | 7.5 | 7.5 | 7.5 | 7.5 | 7.5 |
| Meat-bone meal | 1.5 | 1.5 | 1.5 | 1.5 | 1.5 | 1.5 |
| Calcium carbonate | 1.3 | 1.3 | 1.3 | 1.3 | 1.3 | 1.3 |
| Common salt | 0.2 | 0.2 | 0.2 | 0.2 | 0.2 | 0.2 |
| Premix[*6] | 0.8 | 0.8 | 0.8 | 0.8 | 0.8 | 0.8 |
| Beef tallow | — | — | — | 1.0 | — | 3.0 |
| Component (a) (MCT) | 1.5 | 1.0 | 2.0 | 1.0 | 0.5 | — |
| Component (b): | | | | | | |
| Invention: | | | | | | |
| A | 1.5 | — | — | — | — | — |
| B | — | 2.0 | — | — | — | — |
| C | — | — | 1.0 | 1.0 | — | — |
| Comparison: | | | | | | |
| D | — | — | — | — | 2.5 | — |

[*6] A product comprising amino acids, vitamins, minerals and antibiotics.

TABLE 4

| Component (% by weight) | Test lot I | Test lot II | Test lot III | Test lot IV | Comparison lot I | Comparison lot II |
| --- | --- | --- | --- | --- | --- | --- |
| Corn | 60.5 | 57.5 | 59.5 | 57.5 | 60.5 | 57.5 |
| Milo | 5.0 | 5.0 | 5.0 | 5.0 | 5.0 | 5.0 |
| Soybean cake | 18.8 | 18.8 | 18.8 | 18.8 | 18.8 | 18.8 |
| Fish meal | 7.0 | 7.0 | 7.0 | 7.0 | 7.0 | 7.0 |
| Meat-bone meal | 1.3 | 1.3 | 1.3 | 1.3 | 1.3 | 1.3 |
| Calcium carbonate | 1.5 | 1.5 | 1.5 | 1.5 | 1.5 | 1.5 |
| Common salt | 0.3 | 0.3 | 0.3 | 0.3 | 0.3 | 0.3 |
| Premix[*6] | 0.6 | 0.6 | 0.6 | 0.6 | 0.6 | 0.6 |
| Beef tallow | — | — | — | 4.0 | — | 8.0 |
| Component (a) (MCT) | 2.0 | 4.0 | 3.5 | 2.0 | 1.0 | — |
| Component (b): | | | | | | |
| Invention: | | | | | | |
| A | 3.0 | — | — | — | — | — |
| B | — | 4.0 | — | 2.0 | — | — |
| C | — | — | 2.5 | — | — | — |
| Comparison: | | | | | | |
| D | — | — | — | — | 4.0 | — |

[*6] A product comprising amino acids, vitamins, minerals and antibiotics.

TABLE 5

| | Fresh body weight (g) | Abdominal fat (g) | Abdominal fat/body weight (%) | Feed conversion rate (%) |
| --- | --- | --- | --- | --- |
| Test lot: | | | | |
| I | 3250 | 72.5 | 2.23 (57.9) | 2.01 |
| II | 3310 | 80.3 | 2.43 (63.1) | 1.98 |
| III | 3280 | 74.5 | 2.27 (59.0) | 2.02 |
| IV | 3280 | 91.3 | 2.78 (72.2) | 2.10 |
| Comparison lot: | | | | |
| I | 3190 | 118.6 | 3.72 (96.6) | 2.18 |
| II | 3210 | 123.5 | 3.85 (100) | 2.30 |

Notes;
(1) Abdominal fat/fresh body weight rates given in parenthesis mean the rates calculated by referring the value of the comparison lot II as to 100.
(2) Feed conversion rate:
Feed conversion rate = Feed intake (g)Body weight (g)

While the invention has been described in detail and with reference to specific examples thereof, it will be apparent to one skilled in the art that various changes and modifications can be made therein without departing form the spirit and scope thereof.

What is claimed is:

1. A feed additive for livestock which comprises the following components (a) and (b):
   (a) a triglyceride of a medium-chain fatty acid having 6 to 12 carbon atoms; and
   (b) at least one substance selected from the group consisting of a monoglyceride of a medium-chain fatty acid having 6 to 12 carbon atoms and a diglyceride of a medium-chain fatty acid having 6 to 12 carbon atoms, wherein component (a) and component (b) are present in a weight. ratio of from 10/90 to 90/10.

2. A feed additive of claim 1, wherein said medium-chain fatty acid having 6 to 12 carbon atoms is caproic acid, caprylic acid, capric acid, lauric acid or a mixture thereof.

3. A feed for livestock which comprises from 0.5 to 20% by weight of said feed additive of claim 1.

4. A feed for livestock as claimed in claim 1 wherein said livestock is broiler.

5. A method for preventing protozoiasis of livestock in need of such treatment which comprises the step of feeding to said livestock, prior to infection with disease-causing protozoans, a feed containing an additive comprising the following components (a) and (b):
   (a) a triglyceride of a medium-chain fatty acid having 6 to 12 carbon atoms; and
   (b) at least one substance selected from the group consisting of a monoglyceride of a medium-chain fatty acid having 6 to 12 carbon atoms and a diglyceride of a medium-chain fatty acid having 6 to 12 carbon atoms, wherein component (a) and component (b) are present in a weight ratio of from 10/90 to 90/10.

6. A method of claim 5, wherein said feed is fed to the livestock in an amount such that from 1 to 600 g of said feed additive is fed per day per kilogram of livestock body.

7. A method for treating protozoiasis in livestock infected with disease-causing protozoans comprising the step of feeding to said livestock a feed containing an additive comprising the following components (a) and (b):
   (a) a triglyceride of a medium-chain fatty acid having 6 to 12 carbon atoms; and
   (b) at least one substance selected from the group consisting of a monoglyceride of a medium-chain fatty acid having 6 to 12 carbon atoms and a diglyceride of a medium-chain fatty acid having 6 to 12 carbon atoms, wherein component (a) and component (b) are present in a weight ratio of from 10/90 to 90/10.

8. The method according to claim 6, wherein said method comprises feeding from 1 to 600 g of said feed additive per day per kilogram of livestock body.

* * * * *